United States Patent [19]
Briend et al.

[11] Patent Number: 5,427,104
[45] Date of Patent: Jun. 27, 1995

[54] APPARATUS AND PROCESS FOR INJECTION OF A GAS

[75] Inventors: Robert Briend, Les Clayes En Bois; Jean-Marie Willemot, Sceaux; Hervé Muntlak, Paris, all of, France

[73] Assignee: La Compagnie Francaise de Produits Oxygenes, Paris La Defense, France

[21] Appl. No.: 38,691

[22] Filed: Mar. 29, 1993

[30] Foreign Application Priority Data

Aug. 30, 1991 [FR] France .................. 91 10783

[51] Int. Cl.$^6$ .................................................. A61B 6/00
[52] U.S. Cl. ............................. 128/654; 128/204.25
[58] Field of Search .............. 128/654, 659, 205.11, 128/205.25, 204.25, 655

[56] References Cited

U.S. PATENT DOCUMENTS

| | | | |
|---|---|---|---|
| 3,991,790 | 11/1976 | Russell | 137/819 |
| 4,072,148 | 2/1978 | Munson et al. | 128/205.11 |
| 4,278,110 | 7/1981 | Price et al. | 128/204.24 |
| 4,793,358 | 12/1988 | Kimura et al. | 128/654 |
| 4,991,616 | 2/1991 | Fabregat | 128/205.11 |
| 5,086,767 | 2/1992 | Legal | 128/205.11 |

*Primary Examiner*—Ruth S. Smith
*Attorney, Agent, or Firm*—Young & Thompson

[57] ABSTRACT

Apparatus and process for injection of a gas, preferably carbon dioxide, comprising a source of the gas connected to at least two conduits (C) each provided with a control valve (EV) and a control (Q) of the gaseous flow rate. All of the conduits (C) open into a single channel (B), provided with a three-way control valve (V). The control (Q) of the gaseous flow rate is a calibrated orifice. The control valve (EV) and three-way control valve (V) are electrovalves. The channel (B) is connected to a catheter for injection of the gas into a body. The controls (Q) each permit a different flow rate through the associated control valve (EV), whereby a range of total flow rates of gas into the channel can be achieved by opening and closing selected ones of the controls.

15 Claims, 1 Drawing Sheet

APPARATUS AND PROCESS FOR INJECTION OF A GAS

FIELD OF THE INVENTION

The present invention relates to an apparatus and a process for injection of a gas, particularly carbon dioxide.

BACKGROUND OF THE INVENTION

The optical properties of carbon dioxide are well known and have particularly been used in vascular examination, particularly hepatic and cardiac vascular examination, by means of X-rays.

Until the present, the injection of carbon dioxide, preceding by a fraction of a second the taking of an X-ray, is effected by means of a conventional syringe, for example of the type comprising a piston on which one presses manually, and this adjacent the X-ray beam. The user of the syringe is thus exposed to an important dosage of X-ray.

OBJECTS OF THE INVENTION

A first object of the invention therefore consists in a gas injection device, such as for carbon dioxide, neon or xenon, which permits effecting said injection at a distance and therefore sheltered from harmful radiation.

The invention also permits injecting gas at variable and controlled flow rates and volumes, which permits exploring the proximal and distal regions of the injection site, and this without risk and in a manner that can be automated.

Another object of the invention consists in a process for the injection of a gas, such as carbon dioxide, which can be performed by means of said apparatus.

SUMMARY OF THE INVENTION

The present invention therefore relates to an apparatus for the injection of a gas, particularly carbon dioxide, characterized in that it comprises a source of said gas connected to at least two conduits (C) each provided with a control valve (EV) and with control means (Q) of the gas flow, each of said conduits (C) opening into a single channel (B) provided with a three-way control valve (V).

The present invention will be better understood from the description which follows.

BRIEF DESCRIPTION OF THE DRAWINGS

The figure of the drawing represents an apparatus according to the invention.

DETAILED DESCRIPTION OF THE INVENTION

Figure 1:
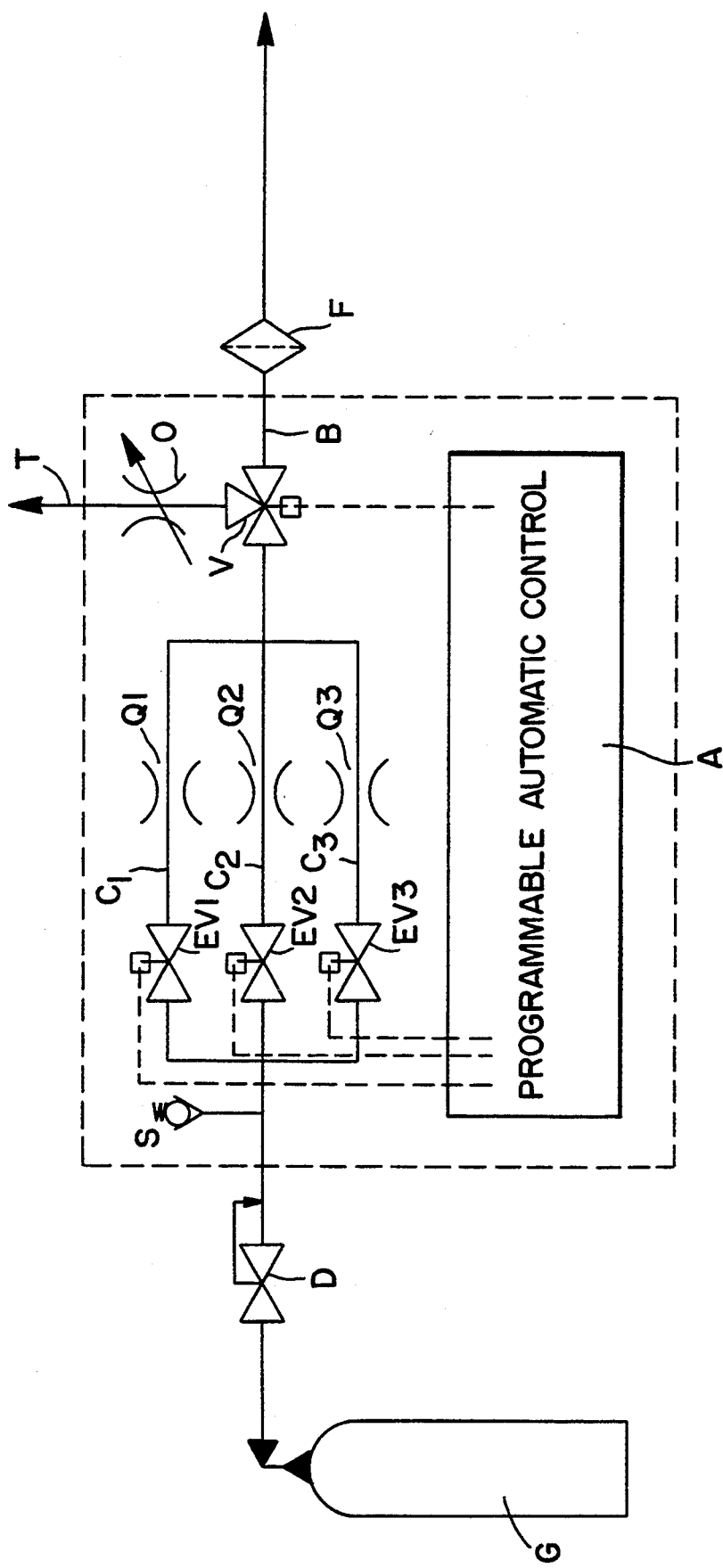

Within the scope of the present invention, the control means (Q) of the gas flow could be means permitting obtention of any selected flow rate.

The selected flow rate may be identical or different for each control means (Q) of the gas flow used. Such a means could for example be a capillary tube, but preferably it consists in a calibrated orifice.

Preferably, each conduit (C) is provided with a control valve (EV) disposed upstream of said control means (Q) of the gas flow. The control valves (EV) and the three-way control valve (V) could be pneumatic valves or preferably electro valves.

Generally, the apparatus of the invention comprises, for example between the gas source and the control valves (EV) a safety valve (S) which can be loaded at a chosen pressure.

The channel (B) can be provided with a filter (F) adapted to stop any non-gaseous material, and at its downstream end, a tubing, such as a catheter, permitting facilitating the injection of the gas into the object or the receiving body.

In a particularly preferred embodiment, the control valves (EV) as well as the three-way control valve (V), are connected to a programmable automatic control (A) which is remotely controlled, of the type comprising at least one microprocessor, a data input stage and a power output stage to actuate the control valves (EV) and the three-way control valve (V). Such programmable automatic control is known per se. The programmable automatic control can be remotely controlled by a conventional control housing, disposed adjacent the operator, thereby preventing the latter from being exposed to harmful radiation, essentially in the case in which the apparatus of the invention is used for the injection of a gas for radiological purposes.

An embodiment is illustrated in the accompanying drawing.

The apparatus shown in this figure comprises a gas source (G), here carbon dioxide, provided with an expander (D) supplying the gas at a selected pressure. The gas source (G) is connected to three conduits, respectively $C_1$, $C_2$ and $C_3$, each provided with a respective electrovalve $(EV_1)$, $(EV_2)$ and $(EV_3)$ and downstream of these latter, calibrated orifices, respectively $(Q_1)$, $(Q_2)$ and $(Q_3)$. The three conduits empty into a channel (B) provided with a three-way electrovalve (V) and a filter (F), and whose downstream end is connected to a catheter (not shown). The three-way electrovalve (V) is here also connected to a conduit (T) opening into the air and provided with a variable orifice draft device (O).

The electrovalves $(EV_1)$, $(EV_2)$ and $(EV_3)$ as well as the three-way electrovalve (V) are connected to a programmable automatic control (A) remotely controlled by a control housing (not shown).

Another object of the invention the present invention consists of a process for the injection of a gas, characterized in that there is introduced continuously said gas at a predetermined pressure into at least two conduits each provided with a control valve and a control means for the gas flow rate, then the gas is passed into a channel into which empties said conduits and which is provided with a three-way control valve which permits selectively and successively sending the gas to the atmosphere or to empty it into the upstream end of the channel, the gas being injected when said three-way valve is positioned such that the gas empties into the upstream end of the channel.

The process of the invention can be practiced by means of an apparatus such as described above. More particularly, when this apparatus is that shown in the figure, the process can be practiced in the following way:

Carbon dioxide, from a gas source (G), is expanded to 4 bars and passes through at least one of the conduits $(C_1)$, $(C_2)$ and $(C_3)$. Of course, it is possible to expand the gas to any other pressure, as needed, but generally speaking, the pressure upstream of the flow rate control means will be at least twice the pressure prevailing downstream of said flow control means. In this way, there is obtained a regular gas flow independent of fluctuations of pressure which can take place downstream of the calibrated orifices; the downstream pressure being ordinarily substantially that prevailing in the body or the object into which the gas is injected. Said body or object is connected to the downstream end of the channel if desired by means of tubing such as a catheter.

The safety valve is loaded to 4.5 bar, such that the carbon dioxide being expanded to a pressure greater than 4.5 bar, the pressure of the gas will be at most 4.5 bar upstream of the calibrated orifices.

The opening or closing of the electrovalves ($EV_1$), ($EV_2$) and ($EV_3$) permits or not the passage of the gas into said conduits ($C_1$), ($C_2$), ($C_3$). These latter being provided each with a calibrated orifice controlling the gaseous flow rate, the opening of said control valves permits a control of the total flow rate of the gas to be injected.

By way of example, there have been selected the calibrated orifices ($C_1$), ($C_2$), ($C_3$) permitting a flow rate, respectively, of 5 cc/sec, 10 cc/sec and 20 cc/sec. One can therefore easily vary the total flow rate according to whether one operas or not one or several of the electrovalves.

The opening and closing of the electrovalve ($EV_1$), ($EV_2$) and ($EV_3$) is effected by means of the programmable automatic control (A) remotely controlled by the control housing.

Different flow rates that can be selected by means of the device shown in the figure are indicated by way of example in the following table.

| Condition of Control Valves | | | Flow Rate |
| --- | --- | --- | --- |
| $EV_1$ | $EV_2$ | $EV_3$ | in cc/sec |
| 1 | 0 | 0 | 5 |
| 0 | 1 | 0 | 10 |
| 1 | 1 | 0 | 15 |
| 0 | 0 | 1 | 20 |
| 1 | 0 | 1 | 25 |
| 0 | 1 | 1 | 30 |

0: closed valve
1: open valve

The gas emerging from the calibrated orifices then passes into the channel (B) and into the three-way electrovalve (V). This latter can be positioned so as to send the carbon dioxide to the atmosphere, if desired after passage through the conduit (T) provided with the variable orifice draft device (O), adjusted such that the pressure of the gas discharged to the atmosphere will be equal to or about that prevailing in the body or object into which the gas is ejected.

If the gas is to be injected, for example into the vascular system so as to take a radiogram, the three-way electrovalve (V) is positioned such that the gas empties into the upstream end of the channel, and passes into the catheter connected to the vascular system.

The change of position of the three-way electrovalve can itself also be controlled from the programmable automatic control and hence remotely. The volume of gas injected with controlled flow rate, depends on the time during which the three-way electrovalve is positioned such that the gas empties into the upstream end of the channel.

This time can itself also be fixed by the programmable automatic control. After a predetermined volume of gas has been injected, the three-way electrovalve is repositioned such that the gas empties again to the atmosphere, several gas injections being adapted to be thus successively made, if desired at variable flow rates. When the gas is injected into the vascular system, the volume of injected gas is conventionally comprised between 50 and 150 cc/injection.

To the extent to which the flow of carbon dioxide is not substantially interrupted during change of position of the three-way control valve, the gas is injected without surge, which is to say without excess passage pressure. Such an excess pressure is particularly undesirable when the gas is injected into a human or animal body, more particularly into the vascular system. It is one of the principal characteristics of the apparatus and process of the invention that these surges are avoided.

Carbon dioxide is a gas preferred in the present invention. However, other gases can be used, among which could be cited xenon and neon.

What is claimed is:

1. Apparatus for the injection of a predetermined volume of a gas into a living body, comprising a source of gas connected to at least two conduits, each conduit including a control valve and a control means for controlling the flow rate of gas through the control valve, all of said conduits opening into a single channel having a three-way control valve, said channel having a downstream end for fluid connection to a tubing for sending the predetermined volume of gas to the living body.

2. Apparatus according to claim 1, wherein said control means is a calibrated orifice.

3. Apparatus according to claim 1, wherein at least one of said control valves and said three-way control valve is an electrovalve.

4. Apparatus according to claim 1, wherein each control valve is disposed upstream of each control means.

5. Apparatus according to claim 1, wherein said channel further includes a filter.

6. Apparatus according to claim 1, wherein said downstream end is fluidly connected to a tubing, said tubing being a catheter.

7. Apparatus according to claim 1, wherein the control valves and the three-way control valve are connected to a programmable remotely controlled automatic control for said valves.

8. Process for the injection of a predetermined volume of a gas into a living body, comprising continuously introducing a gas at a predetermined pressure into at least two conduits, each conduit having a control valve and a control means for controlling the flow rate of gas through the control valve, then passing the gas into a single channel into which empty all said conduits, said channel fluidly connected to the living body and including a three-way control valve which selectively permits sending the gas to the atmosphere or injecting the predetermined volume of gas into the living body, said predetermined volume of gas being controlled according to the time during which the three-way control valve is positioned such that the gas flows toward said living body.

9. Process according to claim 8, wherein the flow rate of the gas entering an upstream end of the channel is effected by opening at least one of said control valves.

10. Process according to claim 8, wherein the pressure of the gas upstream of said control means is at least twice the pressure of the gas downstream of the control means.

11. Process according to claim 8, further comprising remotely controlling the opening of said control valves and the positioning of said three-way control valve.

12. Process according to claim 8, further comprising injecting the gas into the vascular system of a living body.

13. Process according to claim 8, wherein the gas is carbon dioxide.

14. Process according to claim 8, wherein the gas is selected from the group consisting of neon and xenon.

15. Process according to claim 8, further comprising setting said control means so that the flow rate of gas through each control valve is different, whereby a range of total flow rates of gas into the channel can be achieved by opening and closing selected ones of said control means.

* * * * *